United States Patent
Tsushima

(10) Patent No.: US 7,423,062 B2
(45) Date of Patent: Sep. 9, 2008

(54) INSECTICIDAL COMPOSITION

(75) Inventor: Kazunori Tsushima, Sanda (JP)

(73) Assignee: Sumitomo Chemical Company, Limited, Osaka (JP)

( * ) Notice: Subject to any disclaimer, the term of this patent is extended or adjusted under 35 U.S.C. 154(b) by 721 days.

(21) Appl. No.: 10/738,079

(22) Filed: Dec. 17, 2003

(65) Prior Publication Data

US 2005/0137250 A1 Jun. 23, 2005

(51) Int. Cl.
*A01N 53/06* (2006.01)
(52) U.S. Cl. .......................... 514/531; 514/452
(58) Field of Classification Search ................. 514/531, 514/452
See application file for complete search history.

(56) References Cited

U.S. PATENT DOCUMENTS 6,225,495 B1    5/2001  Ujihara et al.

FOREIGN PATENT DOCUMENTS

| DE | 24 22 321 A1 | 1/1975 |
| EP | 0 387 078 A1 | 9/1990 |
| EP | 0 939 073 A1 | 9/1999 |
| EP | 0 962 140 A1 | 12/1999 |
| JP | 6-92807 A | 4/1994 |
| JP | 9-30902 A | 2/1997 |
| JP | 2000-355510 A | 12/2000 |

*Primary Examiner*—Neil Levy
(74) *Attorney, Agent, or Firm*—Panitch Schwarze Belisario & Nadel LLP

(57) ABSTRACT

An insecticidal composition which comprises an ester compound given by formula (1):

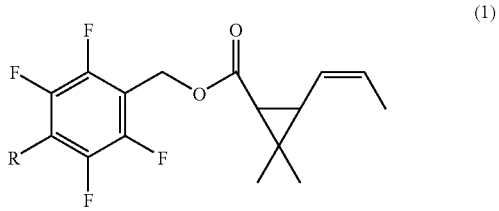

(1)

[wherein R represents a methyl or methoxymethyl group] and 2,4,6-triisopropyl-1,3,5-trioxane as active ingredients, wherein the weight ratio of the ester compound to 2,4,6-triisopropyl-1,3,5-trioxane is 1:4000 to 1:4, is useful for controlling insects, especially insects which are harmful to fabric.

8 Claims, No Drawings

INSECTICIDAL COMPOSITION

FIELD OF THE INVENTION

This invention relates to an insecticidal composition, especially an insecticidal composition suitable for controlling insects which are harmful to fabric or for protecting the fabric from the insects.

BACKGROUND ART

Hitherto, solid insecticidal compounds such as p-dichlorobenzene, naphthalene, camphor and the like have been utilized as fabric protectant. As these compounds tend to be sublimated, it is possible to identify the end point of the fabric protectant easily by the disappearance of the compounds. However, the compounds have a specific smell and the unpleasant odor were often adhered to the protected fabric such as clothes, or they have insufficient effect for controlling insects which are harmful to fabric. On the other hand, empenthrin has been developed as an odorless fabric protectant, but it is difficult to identify the end point of the fabric protectant since the empenthrin is colorless liquid.

SUMMARY OF THE INVENTION

The present invention provides an insecticidal composition which comprises an ester compound given by formula (1):

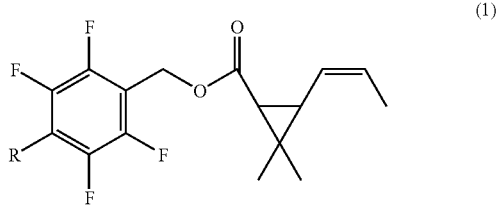

(1)

[wherein R represents a methyl or methoxymethyl group] and 2,4,6-triisopropyl-1,3,5-trioxane as active ingredients, wherein the weight ratio of the ester compound to 2,4,6-triisopropyl-1,3,5-trioxane is 1:4000 to 1:4.

DISCLOSURE OF THE INVENTION

In the present invention, the weight ratio of the ester compound given by formula (1) to 2,4,6-triisopropyl-1,3,5-trioxane in the insecticidal composition is 1:4000 to 1:4, preferably 1:2500 to 1:100 by weight. Said ester compound given by formula (1) is 2,3,5,6-tetrafluoro-4-methylbenzyl 3-(1-propenyl)-2,2-dimethylcyclopropanecarboxylate, 2,3,5,6-tetrafluoro-4-methoxymethylbenzyl 3-(1-propenyl)-2,2-dimethylcyclopropanecarboxylate or a mixture thereof, and it may be any stereoisomer or mixture having insecticidal activity. Said stereoisomers include optical isomers based on the asymmetric carbon atom and geometrical isomers based on the cyclopropane ring and carbon-carbon double bond.

The ester compound given by formula (1) is known in U.S. Pat. No. 6,225,495 and produced according to the description, and 2,4,6-triisopropyl-1,3,5-trioxane is also a known compound and in the market.

The present insecticidal composition is suitable for controlling insects which are harmful to fabric and it is utilized for protecting the fabric from the insects.

When the present insecticidal composition is used for fabric protectant, it is preferably a composition essentially consisting of the ester compound given by formula (1) and 2,4,6-triisopropyl-1,3,5-trioxane. However, it may further contain a component vaporizable at room temperature such as sublimate compound (e.g. p-dichlorobenzene, naphthalene, camphor) and fungicidal compound (e.g. 4-hydroxy-6-methyl-3-(4-methylpentanoyl)-2-pyrone, 3-methyl-4-isopropylphenol, thymol, carvacrol, 4-chloro-3,5-dimethylphenol, 4-chloro-3-methylphenol, hinokitiol). The present insecticidal composition can be prepared by mixing the ester compound given by formula (1), 2,4,6-triisopropyl-1,3,5-trioxane and optionally the other components, melting them at approximately 70 to 200° C., and allowing the mixture to be cooled below approximately 40° C. in a container, optionally further cutting or shaping. The present insecticidal composition can also be prepared by mixing the ester compound, 2,4,6-triisopropyl-1,3,5-trioxane and optionally the other components, and pressed with a tableting machine. Further, the present insecticidal composition can be prepared by dropping the ester compound or its solution to a tablet of 2,4,6-triisopropyl-1,3,5-trioxane. Furthermore, the present insecticidal composition can be prepared by dissolving the ester compound, 2,4,6-triisopropyl-1,3,5-trioxane and optionally the other components in a solvent and impregnating a solid carrier with the solution and drying it.

The insecticidal composition is usually kept in a sealed envelop such as laminated aluminum and the like, the package is torn and the insecticidal composition is taken out to provide the use for controlling the insects which are harmful to fabric.

The insecticidal composition may be used in various ways; usually, it is placed in the vicinity of fabric and for instance, it may be directly placed in a cabinet drawer, or may be packed in an appropriate container and slung up in a wardrobe. The amount of the ester compound given by formula (1) used for controlling the insects or protecting the fabric is usually 0.1 to 50000 mg, preferably 1 to 500 mg per 1 $m^3$ of space. For example, 10 to 2000 mg of the ester compound given by formula (1) are sufficient to give effect for controlling the insects for 6 months in a 0.5 $m^3$ wardrobe. Further, 4 to 400 mg of the ester compound given by formula (1) are sufficient to give effect for controlling the insects for 6 months in a 0.05 $m^3$ drawer.

Examples of said fabric to be protected by the insecticidal composition of the present invention include clothes, underwear, textile, stockings and gloves. Examples of the material of the fabric include animal fibers such as silk, wool, cashmere and mohair; plant fibers such as cotton and hemp; regenerated fibers such as rayon; semi-synthetic fibers such as acetate fiber and triacetate fiber; and synthetic fibers such as nylon, acryl fiber and polyester fiber.

Examples of the harmful insects include *Attagenus unicolor japonicus* (black carpet beetle), *Authrenus verbasci* (varied carpet beetle), *Dermestes maculates* (hide beetle), *Gibbium aequinoctiale, Tinea translucens* (casemaking clothes moth) and *Tineola bisselliella* (webbing clothes moth).

The present insecticidal composition generally has a synergistic effect for controlling insects. In addition, it is easy to identify the end point of the insecticidal composition as the disappearance of the insecticidal composition is easily observed concerning the present insecticidal composition essentially consisting of the ester compound given by formula (1) and 2,4,6-triisopropyl-1,3,5-trioxane.

Though the insecticidal composition of the present invention is suitable for controlling insects which are harmful to fabric or for protecting the fabric from the insects, it is also applicable for controlling the other insects such as mosquitoes, flies, cockroaches and so on; in that case, the ester compound given by formula (1) and 2,4,6-triisopropyl-1,3,5-trioxane may be formulated together with a suitable carrier to various formulations. The dosage of the present insecticidal composition is generally the same as above, namely 0.1 to 50000 mg per 1 $m^3$ of space at the amount of the ester compound given by formula (1). For example, an insecticidal composition consisting of the ester compound given by formula (I) and 2,4,6-triisopropyl-1,3,5-trioxane is placed or hung in the room at the rate of 0.1 to 50000 mg of the ester compound per 1 $m^3$ for controlling mosquitoes and flies.

EXAMPLES

The present invention is explained in more detail by the following examples.

Formulation Example 1

A mixture of 10 mg of 2,3,5,6-tetrafluoro-4-methylbenzyl (1R)-trans-3-(1-propenyl(Z/E=8/1))-2,2-dimethylcyclopropanecarboxylate (hereinafter, referred to as Compound A) and 2000 mg of 2,4,6-triisopropyl-1,3,5-trioxane (hereinafter, referred to as Compound B) was well stirred and pressed with a tablet machine to give a columnar composition (3 cm in diameter and 3 mm in thickness) of the present invention (Composition 1).

Formulation Example 2

A mixture of 10 mg of Compound A and 4000 mg of Compound B was well stirred and pressed with a tablet machine to give a columnar composition (3 cm in diameter and 6 mm in thickness) of the present invention (Composition 2).

Formulation Example 3

A 100 µl of acetone solution containing 50 µg of Compound A and 100 mg of Compound B was dropped onto a 2 cm×2 cm filter paper and dried to give a composition of the present invention (Composition 3).

Formulation Example 4

One milligram (1 mg) of Compound A and 2000 mg of Compound B are put into a 30 ml-volume of vial and melt them with shaking under heating by a heat gun, and then allowed to cool to room temperature for one hour to give the composition of the present invention (Composition 4.

Formulation Example 5

The same procedure as Formulation Example 4 is carried out, except that 5 mg of Compound A is used in place of 1 mg, to give the composition of the present invention (Composition 5.

Formulation Example 6

The same procedure as Formulation Example 4 is carried out, except that 10 mg of Compound A is used in place of 1 mg, to give the composition of the present invention (Composition 6).

Formulation Example 7

The same procedure as Formulation Example 4 is carried out, except that 20 mg of Compound A is used in place of 1 mg, to give the composition of the present invention (Composition 7).

Formulation Example 8

The same procedure as Formulation Example 4 is carried out, except that 50 mg of Compound A is used in place of 1 mg, to give the composition of the present invention (Composition 8).

Formulation Example 9

The same procedure as Formulation Example 4 is carried out, except that 100 mg of Compound A is used in place of 1 mg, to give the composition of the present invention (Composition 9).

Formulation Example 10

The same procedure as Formulation Example 4 is carried out, except that 200 mg of Compound A is used in place of 1 mg, to give the composition of the present invention (Composition 10).

Formulation Example 11

The same procedure as Formulation Example 4 is carried out, except that 300 mg of Compound A is used in place of 1 mg, to give the composition of the present invention (Composition 11).

Formulation Example 12

The same procedure as Formulation Example 4 is carried out, except that 400 mg of Compound A is used in place of 1 mg, to give the composition of the present invention (Composition 12).

Formulation Examples 13-21

The same procedures as Formulation Examples 4-12 are carried out, except that 2,3,5,6-tetrafluoro-4-methoxymethylbenzyl (1R)-trans-3-(1-propenyl(Z/E=8/1))-2,2-dimethylcyclopropanecarboxylate is used in place of Compound A, to give the compositions of the present invention (Compositions 13-21).

Reference Formulation Example 1

One hundred milligrams (100 mg) of empenthrin and 2000 mg of Compound B were put into a 30 ml-volume of vial and melt them with shaking under heating by a heat gun, and then allowed to cool to room temperature for one hour to give a reference composition (Reference Composition 1).

Reference Formulation Example 2

Fifty milligrams (50 mg) of empenthrin and 2000 mg of p-dichlorobenzene were put into a 30 ml-volume of vial and melt them with shaking under heating by a heat gun, and then allowed to cool to room temperature for one hour to give a reference composition (Reference Composition 2).

Reference Formulation Example 3

A 100 µl of acetone solution containing 50 µg of Compound A was dropped onto a 2 cm×2 cm filter paper and dried to give a composition of the present invention (Reference Composition 3).

Reference Formulation Example 4

A 100 µl of acetone solution containing 100 mg of Compound B was dropped onto a 2 cm×2 cm filter paper and dried to give a composition of the present invention (Reference Composition 4).

Test Example 1

About 2 mg of each of Composition 9, Reference Composition 1 and Reference Composition 2 was put on a filter paper and allowed to stand at room temperature for one hour, and then the status of each of the compositions was observed. The results are given in Table 1.

TABLE 1

| Compositions | Status |
|---|---|
| Composition 9 | G |
| Reference Composition 1 | B |
| Reference Composition 2 | B |

G means a status of good crystallization.
B means a status wherein the crystals are melted.

Test Example 2

Wool muslin cloth (2 cm×2 cm) and 10 middle-instar larvae of webbing clothes moth (*Tineola bisselliella*) were put on the bottom of a plastic container (10 cm in a bottom diameter, 12.5 cm in a top opening diameter, 9.5 cm in height and 950 cm$^3$ of volume), and the opening of the container was covered with a 32-mesh nylon net. Composition 1 was put on the nylon net and put the lid on the container and sealed. After allowing to stand at 25±2° C. for 7 days, the lid was taken off and the percent moribund was calculated. Further, the degree of the eaten damage of the wool muslin cloth was observed. The standard of the degree was as follows:

| | |
|---|---|
| +++ | Remarkably damaged |
| ++ | Severely damaged |
| + | Damaged |
| ± | Slightly damaged |
| − | No damaged |

Furthermore, the same test as the above was carried out except that Composition 2 was used in place of Composition 1. The results are given in Table 2.

TABLE 2

| Tested compositions | Percent moribund (%) | Damage |
|---|---|---|
| Composition 1 | 100 | − |
| Composition 2 | 100 | − |
| No treatment | 0 | +++ |

Test Example 3

Wool muslin cloth (2 cm×2 cm) and 10 middle-instar larvae of webbing clothes moth (*Tineola bisselliella*) were put on the bottom of a plastic container (10 cm in a bottom diameter, 12.5 cm in a top opening diameter, 9.5 cm in height and 950 cm$^3$ of volume), and the opening of the container was covered with a 32-mesh nylon net. Composition 3 was put on the nylon net and put the lid on the container and sealed. After allowing to stand at 25±2° C. for 7 days, the lid was taken off and the percent moribund was calculated. Further, the degree of the eaten damage of the wool muslin cloth was observed. The standard of the degree was as follows:

| | |
|---|---|
| +++ | Remarkably damaged |
| ++ | Severely damaged |
| + | Damaged |
| ± | Slightly damaged |
| − | No damaged |

Furthermore, the same test as the above was carried out except that Reference Composition 3 and 4 were used in place of Composition 1. The results are given in Table 3.

TABLE 3

| Tested compositions | Percent moribund (%) | Damage |
|---|---|---|
| Composition 3 | 100 | − |
| Reference Composition 3 | 55 | ± |
| Reference Composition 4 | 0 | +++ |

What is claimed is:

1. An insecticidal composition which comprises an ester compound given by formula (1):

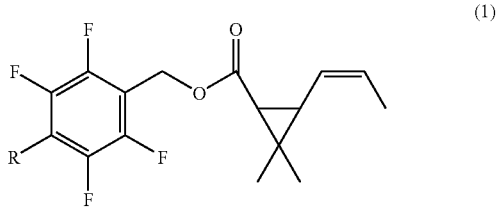

wherein R represents a methyl or methoxymethyl group;
and 2,4,6-triisopropyl-1,3,5-trioxane as active ingredients, wherein the weight ratio of the ester compound to 2,4,6-triisopropyl-1,3,5-trioxane is 1:4000 to 1:4.

2. The insecticidal composition according to claim 1, wherein the weight ratio of the ester compound to 2,4,6-triisopropyl-1,3,5-trioxane in the insecticidal composition is 1:2500 to 1:100 by weight.

3. The insecticidal composition according to claim 1, wherein the R of the ester compound is a methyl group.

4. The insecticidal composition according to claim 1, wherein the R of the ester compound is a methoxymethyl group.

5. The insecticidal composition according to claim 1, wherein the composition consists essentially of the ester compound and 2,4,6-triisopropyl-1,3,5-trioxane.

6. A method for controlling insects which comprises applying the insecticidal composition described in claim 1 to the insects.

7. The method according to claim 6, wherein the insects are insects which are harmful to fabric.

8. A method for protecting fabric which comprises placing the insecticidal composition described in claim 1 in a vicinity of the fabric.

* * * * *